United States Patent [19]

Mayfield

[11] Patent Number: 5,501,973
[45] Date of Patent: Mar. 26, 1996

[54] TREATMENT FOR CONTAMINATED MATERIAL

[76] Inventor: Thomas B. Mayfield, 15417 Chichester, Houston, Tex. 77040

[21] Appl. No.: 247,002

[22] Filed: May 20, 1994

Related U.S. Application Data

[63] Continuation-in-part of Ser. No. 927,147, Aug. 7, 1992, abandoned.

[51] Int. Cl.$^6$ ............... C12N 1/00; C12N 1/38; B09B 3/00; C05F 11/08
[52] U.S. Cl. ............ 435/244; 435/243; 435/262.5; 71/6; 71/11; 71/23; 71/24
[58] Field of Search .................. 435/262.5, 262, 435/243, 244; 71/6, 11, 23, 24, 34

[56] References Cited

U.S. PATENT DOCUMENTS

| | | | |
|---|---|---|---|
| 3,630,710 | 12/1971 | Frederickson | 71/23 |
| 3,999,607 | 12/1976 | Pennington et al. | 166/259 |
| 4,097,244 | 6/1978 | Burk | 201/17 |
| 4,272,251 | 6/1981 | Beckberger et al. | 201/17 |
| 5,133,625 | 7/1992 | Albergo et al. | 405/263 |
| 5,136,954 | 8/1992 | Fetaz et al. | 111/123 |
| 5,143,481 | 9/1992 | Schumacher | 405/129 |
| 5,148,757 | 9/1992 | McCrossan | 110/216 |
| 5,399,267 | 3/1995 | Wang et al. | 210/604 |

OTHER PUBLICATIONS

U.S. Official gazette entry for U.S. Pat. No. 5,169,263, 8 Dec. 1992.
"Product Description Microbe–Lift," Ecological Laboatories, Inc., 1991.
"These Germs Work Wonders," Reader's Digest, Jan. 1991, pp. 83–86.
"The Role Of Soil Microorganisms In Increasing Agriculture Productivity," Worne, 1978, Int'l Conf. on Bio Resource Potential for Development.
"Bacteria prefer to dine in swanky places," Brewster, Soils, Jun. Junly 1993, pp. 46–49.
"Probiotics Enhance Remediation Efforst," Brewster, Environmental Protection, Nov. 1993, pp. 28–32.
"Projects Prove Bioremediation Viable," Brewster, The American Oil And Gas Reporter, Mar. 1994, pp. 38–44.

*Primary Examiner*—Michael G. Wityshyn
*Assistant Examiner*—T. J. Reardon
*Attorney, Agent, or Firm*—Guy McClung

[57] ABSTRACT

A treatment composition for treating contaminated material is disclosed which has water, coal, and an alkali metal carbonate. In another aspect an additional ingredient is a seaweed derivative. A method for making such a treatment composition for treating contaminated material has been developed which includes introducing water into a first tank, blending in alkali metal carbonate in the first tank with the water to form a first composition, adding coal to the first composition and blending them together forming a base composition, introducing one half of the base composition from the first tank into a second tank, introducing an amount of seaweed derivative into the second tank equal in volume to the amount of base composition in the second tank, and blending the contents of the second tank together producing the treatment composition. Methods and materials for soil treatment have been developed in one aspect for remediating hydrocarbon and/or brine contaminated soils; in one embodiment, material having water, soft coal, potash and, if desired, algin extract is applied to the soil; in one embodiment microorganisms are added to the soil.

8 Claims, No Drawings

TREATMENT FOR CONTAMINATED MATERIAL

RELATED APPLICATION

This is a continuation-in-part of U.S. application Ser. No. 07/927,147 filed on Aug. 7, 1992, now abandoned entitled "Soil Treatment" and co-owned with this application for patent.

BACKGROUND OF THE INVENTION

1. Field of the Invention

This invention is related to treatment of contaminated material; to compositions for treating contaminated material; to soil treatment and, in particular aspects, to soil remediation and to methods for reclaiming polluted earth.

2. Description of Related Art

The prior art is replete with materials and methods for treating contaminated material and for soil treatment that include fertilizers, laboratory produced microbes and microorganisms, and various chemical and mechanical reclamation methods. There are numerous problems with the prior art materials and methods. Scientifically produced non-natural microbes and microorganisms do not have a history—what they will evolve to in the future is unknown as is the totality of their effects. Several prior art methods require total removal of contaminated soil to a remote treatment site. This can be time consuming, and expensive. Such methods may also result in another environmentally unacceptable substance or by-product.

SUMMARY OF THE PRESENT INVENTION

The present invention, in certain embodiments, discloses compositions for treating contaminated material, including but not limited to liquids, soil or rocks contaminated with hydrocarbons and/or metals. In one aspect the treating composition is applied to soil or other contaminated material in situ. In another aspect the contaminated material is removed from a contaminated site and is treated batchwise in a tank or other container. In certain preferred embodiments the contaminated material and/or the treating material is aerated during treatment.

The treating composition is made by combining water, coal, and an alkali metal carbonate. A seaweed derivative is an additional preferred ingredient. The ingredients are combined as described below. In one preferred embodiment of a method for producing treating material, the composition in a mixing tank is recirculated from a bottom of the tank to a top of the tank. In another preferred embodiment the recirculating composition is homogenized in an in-line unit prior to re-introduction to the top of the tank. Recirculation and/or homogenization produces a composition which is richer in organic acids (e.g. but not limited to humic, fulvic, ulvic, polyuronic, and alginic acids).

In certain embodiments the compositions produced according to methods of this invention have the characteristics of a liquid solution. In certain embodiments the coal ingredient is initially powderized soft coal in the form of a very fine powder (like talcum powder). In certain embodiments dehumidification of such solutions produces a powder according to this invention which, upon subsequent mixture with water or addition to contaminated material, produces a liquid solution useful in treatment methods according to this invention. In other embodiments the powder is applied in situ or batchwise and water is added to the powder.

Application of treating compositions as described below to contaminated material results in a reduction in hydrocarbons and/or metals, including heavy metals. The present inventor is unaware of the chemical mechanisms and conversions, if any, that explain these results; but without committing to any theory or explanation, the present inventor believes that application of his compositions results in bioremediation of contaminated material and that does more than add chemical fertilizers, microbes and aeration and that contaminated material or soil is first detoxified to provide an environment that promotes expansion of an indigenous microbial colony so the microbes function at their optimum capabilities without being hindered by harmful chemical and non-chemical reactions. Probiological remediation technology using EPA testing methods indicates that hydrocarbons (gasoline, diesel, waste oil, crude, etc.) go through an abiotic transformation process whereby hydrocarbon chains are lengthened and side chains are removed from complex alicyclic and polyaromatic carbon chains. This, in turn, allows for easier microbial degradation of petroleum compounds and reduces volatization of light organic compounds. Organic compounds such as compositions according to this invention are also believed to act on contaminated material or soil particles (sand, silt and clay). The compounds are comprised of carbohydrates, amino acids, fatty acids, proteins, polysaccharides and other elements that have been freed from ancient plants (e.g. coal) and microbial tissues, Certain compounds according to the present invention are predominantly long chain organic acids like humic, fulvic, ulmic, alginic and polyuronic. It is believed that the polysaccharides formed bind the soil particles together, resulting in increased aeration and moisture holding capabilities of the soil, both of which are beneficial for biological growth and that cation exchange capacities release valuable nutrients for plant and microbial usage and add substantially to the health of the soil. It is further believed that degradation of petroleum products (hydrocarbons) by microorganisms involves the conversion of energy stored as petroleum hydrocarbon chains into microbial byproducts such as water, carbon dioxide, cellular biomass, organic matters, organic acids and other beneficial inorganic compounds and elements. A probiological approach according to the present invention is believed to use beneficial organic materials to create an environment in which microorganisms perform natural remediation functions efficiently and as a result, an environment which supports and promotes the growth of contaminant degrading microbes (such as Rhodopseudomonas, Rhodospirillum, Thiobacillus novellus, Thiobacillus Thiooxidans, Thiobacillus denitrificans, Pseudomonas fluorescens, Alcaligenes denitrificans, Flavobactrim aquatile, Flavobactrim oceanosedimentum, Nitrobacter winogradskyi, Nitrosomonas europaea, Serratia Liquifaciens, Rhizobium, and Actinomycetes) is produced. It is also believed that when specific organic acid complexes (such as humic, fulvic, ulmic, polyuromic, and alginic) as in certain compositions of the present invention are applied to an environment affected by petroleum and/or metal contamination, the contaminants are pulled from the matrix of the saturated soil particles without the aid of surfactants or other chemical components and the contaminant then becomes a readily available food source for microbial assimilation as the organic complex binds to the contaminants.

The present invention, in one embodiment, teaches a bioremediation material for soil and a method for using the material. Biodegradation is a natural process in which bacteria consume petroleum hydrocarbons and reduce them to biomass and carbon dioxide. Required for such a process is a food supply (the hydrocarbons), oxygen, a suitable media and an adequate supply of living microorganisms that are acclimated to the environment. Material according to this embodiment of the invention is a mixture of water, coal (preferably soft coal), and an alkali metal carbonate, most preferably potash (preferably flaked potash). A seaweed derivative, e.g. algin extract is preferred as an additional ingredient, e.g. SP 7008 commercially available from Vartchem, Inc. Baytown, Tex. The resulting mixture is a water soluble concentrated material in liquid form that stimulates a very rapid growth of naturally occurring microorganisms. Such microorganisms may have mutated over time to accommodate a hydrocarbon contaminated environment. By increasing their population, the consumption of the hydrocarbons is proportionally increased causing natural bioremediation to continue at an efficient rate until the food supply is exhausted, there is a depletion of oxygen, and/or the temperature of the soil falls below a certain level, e.g. about 2° C. When the hydrocarbon food supply is exhausted, the microorganisms die leaving naturally occurring fatty acids and carbon dioxide.

In one application method according to this invention, concentrated nutrient is diluted with water and applied to a contaminated area. Dilution may vary depending on the extent of contamination. The method of application may include spraying on the surface of contaminated soil, tilling into the soil, or injection into sub-surface contaminated soil and underneath permanent structures. An adequate oxygen supply may be provided for the microorganisms to maintain an aerobic state, however, bioremediation will proceed in an anaerobic state, but at a much slower rate. The lapsed time for remediation will vary depending on the concentration of the hydrocarbon contaminants, the initial population of microorganisms, porosity of the soil, oxygen supply and the temperature. Typically a contaminated area can be bioremediated in 30 to 90 days.

The circumstances of some contaminated sites require immediate removal and replacement of contaminated soil regardless of interruption to business and cost. A less expensive option than moving the contaminated soil to a land fill is to contain it in berms, bioremediate according to this invention, and return the soil to a local useful purpose. Methods and materials according to this invention are very effective on areas that have been contaminated for sufficient time to allow the naturally occurring microorganisms to adapt to their new petroleum food supply, usually 3 to 6 months. If remediation is to start immediately following a petroleum spill, a supply of hydrocarbon degrading microorganisms may be applied at the spill site; otherwise, the native microorganism population initially affected by the contamination may be significantly depleted and several months may lapse before they adapt to their petroleum rich environment. In either case, nutrient, according to this invention, increases the microorganism population and accelerates the bioremediation process.

In another embodiment of the present invention, the material is a solution of water, soft coal and flaked potash, with algin extract as a preferred additional ingredient. This mixture frees molecularly bound sodium in the soil, i.e. it buffers the salt resulting in more aerable permeable soil. Application of this liquid mixture creates an environment for ion exchange that buffers salt, and inhibits the osmotic action normally associated with salt, e.g. sodium chloride contamination. Restoration of the ecological balance allows revegetation of fields, pastures or industrial sites. The amount of material required is dependent upon the area to be remediated and on the levels of salts, e.g. sodium chloride, present in the soil. Since remediation may begin immediately upon application of the material, many sites are restored within days which allows seeding or planting to follow without significant loss of growing season. Abused soil can benefit from an application of fertilizer as a prelude to restoration of the vegetation. Following remediation, any crop applicable to the growing season may be grown. If the subject land is deficient in available ions (e.g. calcium ions) for the ion exchange, an application of an ion-donor and ion-rich solution may be used; e.g. a solution that is about 40% water and about 60% calcium nitrate by weight (the calcium nitrate dissociating in solution to provide calcium ions).

In another embodiment of the present invention the material is a mixture of water, soft coal, flaked potash and, as an additional preferred ingredient, a solution with long chain organic acids, e.g. algin extract, a seaweed derivative; e.g. commercially available SP7008 has alginic acid, polyuronic acid, and plant sucrose. This mixture is applied to agricultural soil to accelerate many natural earth processes. Nature uses decaying organic matter to provide a source of nitrogen to the soil, energy for microorganisms and chelating agents for micro-nutrients. The addition of organic matter to the soil improves soil structure by increasing tilth, friability and aeration, thereby increasing moisture retention and improving drainage. Components of organic matter stimulate a plant growth hormone and increase trace element uptake. Material according to this invention accelerates these natural processes, and through soil improvements, produces healthier plants.

In another embodiment of this invention a mixture of water, coal, sodium carbonate, e.g. soda ash or causticized soda, is applied to petroleum contaminated soil. The growth of naturally occurring remediating microorganisms is stimulated and the soil is remediated, e.g. over a period of weeks.

In another embodiment of the present invention application of a mixture according to this invention results in the breaking of bonds which bond elements, e.g. metals such as iron, manganese and zinc, to soil constituents to make these elements available for plant uptake.

In another embodiment of the present invention a mixture of water, coal, and an alkali metal carbonate, e.g. flaked potash, with or without a solution of long chain organic acids and plant sucrose, is applied to ant mounds. In a short time period the ants leave the mound and re-locate to a non-treated area.

In one particular embodiment of this invention a relatively concentrated solution of material according to this invention is applied to plants to precipitate such fast growth that the plant dies. One application mode is foliar; others include spraying, tilling, or injection.

In another embodiment of this invention a method is provided for producing crops, e.g. but not limited to vegetables, which have a relatively longer shelf life than crops produced by prior art methods; the method including treatment of the soil in which the crops are grown as described herein with materials disclosed herein.

It is, therefore, an object of at least certain preferred embodiments of the present invention to provide:

New, useful, unique, efficient, nonobvious and effective materials, compositions, and methods for treating contaminated materials, liquids, soils, and rocks;

Such compositions and methods for treating materials contaminated with hydrocarbons and/or metals including heavy metals;

New, useful, unique, efficient, safe and effective materials and methods for soil treatment and for bioremediation of contaminated earth;

Such materials and methods for buffering salts in polluted soil;

Such materials and methods for increasing the agricultural productivity of soil;

Such methods and materials for stimulating plant nutrient uptake;

Such methods and materials for producing crops with increased shelf life after harvesting;

Such materials and methods to free trace elements, e.g. metals in metal compounds in soil constituents;

Such materials and methods for application to ant mounds; and

Such materials and methods for effecting accelerated plant growth rates either for increased productivity or for plant destruction.

DESCRIPTION OF EMBODIMENTS PREFERRED AT THE TIME OF FILING FOR THIS PATENT

Example 1

In one preferred embodiment of the present invention, preferably a fiberglass tank or a conventional stainless steel sweep agitation and recirculation tank (the "first" tank) is filled with about 3,776 pounds of untreated water at, most preferably, about 90 degrees Fahrenheit temperature (with a preferred range of about 72 to about 110 degrees Fahrenheit). The sweep agitation is placed in motion and about 205 pounds of flaked potash is introduced into the water and thoroughly blended. About 1200 pounds of soft, low grade powdered bituminous coal is added into the water/potash solution and agitation is continued. Recirculation is begun. Agitation and recirculation are continued throughout the process for, most preferably, approximately seventy-two (72) hours for completion. (Although a preferred lower limit is 24 hours and a preferred upper limit is 120 hours.) This produces a base solution. The base solution in process is analyzed at forty-eight hour, sixty hour and seventy-two hour intervals for the percentage of humic acid present in the solution. The process is preferably complete when the percentage of humic acid is between about 10% to about 30% and most preferably between about 23% and about 26%. When the solution is in process it is preferred to homogenize the entire solution during recirculation.

The base solution is cooled and the pH is measured. The pH is most preferably between 7.0 and 9.0.

A second tank (tank two) is now filled with an equal amount of algin extract solution in volume to the contents of the first tank.

Into a third tank (tank three) is introduced one half of the total volume/gallonage of the solution in the first tank. Agitation is begun and an equal amount of algin extract solution from tank two is added to the third tank. This results in a first solution mixture which can be used as is or can be combined with other ingredients to formulate additional products according to this invention.

Example 2

A second solution is produced according to this invention by taking an amount of the first solution (see Example 1 above) and diluting it with water. Preferably the first solution is diluted so that the resulting second solution is not harmful, is not too "hot" for application to plants. In one embodiment dilution with about 35% water by volume produces an acceptable second solution. Also any sediment remaining in the first tank (tank one, Example 1) may be added to this second solution. A pH of 7.0 is preferred for the second solution.

Example 3

A third solution according to this invention is produced by combining the base solution from Example 1 with a long-chain-organic-acid-plant sucrose solution.

In one embodiment three parts of base solution are combined with one part algin extract solution.

It is preferred (in certain embodiments of mixtures according to the present invention) that they be prepared at such concentrations and at such temperatures that a super-saturated solution is produced. It is also preferred that greater than normal saturation be achieved by re-adding whatever does not go into solution in a first tank into a subsequent mixing tank.

IN SITU APPLICATION

Appropriate in situ bioremediation according to certain embodiments of the present invention takes into account the general ecology of the area, the soil chemistry and the amount and type of contaminating material to be remediated. Each site may require a separate assessment because conditions are different at each site. The primary objective when planning remediation is to bring together the substrate contaminants, indigenous microorganisms, water for dilution and transport with the proper amount of material according to this invention for the purpose of increasing the population of the indigenous microorganisms. The microorganisms will, in turn, consume contaminants over time.

Study of a site for bioremediation may include a general description of the geography of the site, subsurface geology, soil pH, oxygen exchange rate, water table depth and direction of flow, a defined area of contamination, identity and amount of pollutants, rainfall, temperature, microbial population and any pertinent historical data.

Application of material according to this invention stimulates biological activity with hydrocarbons which produces an emulsion resulting from the fatty acids being produced by hydrocarbon decomposition. This emulsion further enhances biological activity by increasing oil to water contact. The rate of biodegradation can be directly related to the oil/water surfaces. Application of the material may be topical, subsurface, or incorporative. Topical application is used, preferably, at sites with hydrocarbon contamination less than about 12 inches from the surface. The material produced as in Example 1 is diluted one part to nine parts of water for coverage and soil penetration. In areas of heavy contamination, dilution may be reduced to one part of material to five parts of water to minimize solution runoff.

Incorporative application is used, preferably, for sites contaminated with hydrocarbons to not more than 23 inches in depth. Incorporation may be accomplished e.g. by tilling or disking. One part of material is mixed, preferably, with about five to about fifty parts of water. One-half of the solution is applied, preferably, prior to incorporation and the remainder after incorporation.

When the area of contamination is more than two feet below the surface, subsurface injection is recommended. This may be done in addition to topical application. Using the information from a contamination survey, a grid pattern is determined for injection holes, based on the soil density.

Typical hole density is one every five feet in dense clay and twenty feet in sand. One part of treatment material is mixed with about five to about fifty parts of water. The solution is fed into the injection holes periodically, e.g. once every third day, until saturation is evidenced for the first two weeks of treatment. It is preferred that a continuous flow of low pressure air (1–3 psi) be injected into the holes in order to maintain an aerobic state. In one embodiment it is preferred that pure oxygen be injected continuously during the remediation process. In another embodiment liquid hydrogen peroxide is injected intermittently (e.g. once every three to five days) to serve as a source for oxygen to sustain increased activity. (Such injections my be beneficial with any method according to this invention).

TEST RESULTS

TEST 1

Approximately 340 cubic yards of soil was found to be contaminated with unleaded gasoline and diesel fuel in the vicinity of the underground storage tanks at a retail service station. One unleaded gasoline tank had been recently overfilled causing contamination of soil between two tanks. The diesel contamination was due to a minor fuel line leak. A report from an independent testing laboratory showed a high level of 494 PPM TPH (total petroleum hydrocarbons) in the "hottest" sample with an average of 385 ppm TPH throughout the contaminated soil.

A plan of remedial action for this site included moving the contaminated spoil to the surface and allowing the sun and wind to degrade the contaminants to a level that would permit the spoil to be returned to the excavation.

Heavy duty visqueen fabric was placed on a cleaned driveway area and approximately 340 cubic yards of contaminated spoil was moved to the surface and placed on the visqueen. Extra visqueen was pulled up around the sides and ends of the contaminated spoil and imported clean spoil was bermed around the contaminated spoil to form a containment. The visqueen was then pulled down and anchored over the clean spoil forming a barrier or liner between the clean and contaminated spoils. The bermed area was approximately 30 feet×50 feet with the spoil stacked 6 feet high.

Thirty days after the bermed spoil was in place approximately ⅓ of the spoil was treated with material as in Test 2, below. Material was diluted 1 part concentrate to 10 parts of water to make 31 gallons of solution. One application of solution was sprayed over the surface of the designated treated area. An independent laboratory took samples 50 days after treatment of the untreated and treated spoil. Remediation was 4 to 5 times more effective after 50 days than the results of normal evaporation of the untreated area. Average TPH content of the spoil at the beginning of remediation was 385 ppm. There were three minor rains on the contaminated spoil that totalled 1⅞".

The following table lists the TPH levels (PPM) on day 50 after treatment.

| Lab Sample Number | Sample Depth | TPH Treated | TPH Untreated |
|---|---|---|---|
| #1 | 1.0' | 82.1 | |
| #2 | 1.0' | 24.2 | |
| #3 | 1.0' | 23.4 | |
| #4 | 1.0' | | 127.9 |
| #5 | 1.0' | | 112.7 |
| #6 | 1.0' | | 232.0 |
| #7 | 2.5' | | 145.3 |
| #8[1] | 3.5' | | 39.7 |
| #9[2] | 3.5' | | 123.5 |

Note:
[1] Sample #8 was under sample #3
[2] Sample #9 was under sample #6.

The spoil was bermed for 30 days prior to the decision to add material according to this invention Therefore, day 50 after treatment was approximately 80 days since the spoil was bermed. The sample data reflects the heterogenous disbursement of the hydrocarbon contamination.

One treatment of the spoil accelerated the expansion of the microorganism population in the spoil sufficiently to accelerate the natural bioremediation process almost 400%. Since the material solution could have been injected into the contaminated spoil in situ, the remediation process could have been completed at a fraction of the cost.

TEST 2

A polluted compressor station had the following contaminated sites:

Hydrocarbon contamination: Sites 1,2,3, & 4

Brine contamination: Site 5

Sites #1 and #2 were primarily clay fill with old contamination of the surface area to a depth of less than twelve inches (12"). Sites #3 and #4 were also clay fill but had surface water/sludge content. Site #5 was heavy black land with salt levels in excess of 12.8 meq/100 g and was devoid of Vegetation. Samples were taken at all sites and initial contaminated values were determined. ("meg" means milliequivalents)

Sites #1 and #2 were treated with material according to this invention at a rate of one gallon per four cubic yards of contaminated soil. The material comprised a mixture of water, soft coal and causticized soda; about 15 parts water, about 5 parts coal, and about 2 parts causticized soda. The material was applied topically in a solution of one part to four parts water. Site #3 was treated like sites #1 and #2 with one exception: the material was applied at a rate of one gallon to eight cubic yards of contaminated soil. It was also applied topically without benefit of incorporation. Site #4 was left in a virgin state and was not disturbed except for sample collection during supervision. Site #5 was treated with the material at a rate of one gallon to ten cubic yards of contaminated soil and was applied topically without incorporation. The initial survey indicated that calcium was present, allowing the material to effect an ion exchange with the sodium molecule.

At Site #1 initial TPH content was about 6600 parts per million (PPM) (mg/kg) TPH and declined to 130 or 225 PPM TPH in 37 days, according to the most favorable test result. Analysis showed 38.6 mg/kg TPH (remediated) on the 56th day of the project.

Site #2 began at a TPH content of 590 PPM TPH and increased to 4300 mg/kg TPH remediated. On the 56th day, analysis showed a value of 7.2 PPM TPH. The site was then tilled for esthetic purposes.

Site #3 had TPH values of 1000 TPH mg/kg at inception and increased to 9200 TPH mg/kg in nine days due to suspected additional contamination. This site was difficult in that suspected recontamination occurred at least three times during the remediation. The TPH level fell to a low of 188.4 mg/kg. The site was given an additional treatment 14 days following initial application, at a rate of one gallon of product per 25 cubic yards. The material was applied topically in a solution of one part material to six parts water. Incorporation was not utilized.

Site #5 was brine contaminated and vegetation was absent. The initial sample analysis showed a level of 12.9 meq/100 g. The initial site survey indicated enough calcium present in the soil to effect an ion exchange necessary to buffer the salts. Material as described above was applied topically without incorporation at a rate of one gallon to ten cubic yards of brine contaminated soil. The material was applied in a solution of one part material to two parts water (this solution may be one to ten). The laboratory analysis was 5.7 meq/100 g within 37 days. An analysis of 8.0 meq/100 g was the initial goal for remediation. After 56 days, it was decided to apply a second application of material and incorporate into the soil, the objective being a substantial reduction below the achieved level of 5.7 meq/100 g since remediation was accomplished in situ in 37 days. Rye grass seeds were broadcast on the 68th day to further allow visual proof of the efficacy of this invention. The grass grew well.

TEST 3

Gasoline-contaminated soil (clay and sand) removed from a service station were treated with first solution material as produced in Example 1 above. The excavated contaminated soil was placed on four mil poly film to a depth of 18 to 24 inches. The contaminated soil was then treated with the material diluted 10 parts water to one (1) part material. This was sprayed until the soil was well wetted; then the entire area was plowed with a dozer—vertically, horizontally and at 45 degree angles. As the plowing was performed, the material was sprayed to wet the exposed areas. The initial TPH of the soil was over 1000 TPH and was remediated to a TPH in the 36 to 100 ppm range with BTEX (Benzene, Toluene, Ethylbenzene, Xylene) at a minimum or less detectable level.

| DATE | | TPH READING, ppm |
|---|---|---|
| | CLAY SOIL PORTION | |
| 1ST DAY | VOM Meter | 900 |
| 2ND DAY (24 HRS) | VOM Meter | 160 |
| 3RD DAY (72 HRS) | Lab Analysis | 100 |
| | SAND PORTION | |
| 1ST DAY | VOM Meter | 900 |
| 2ND DAY | VOM Meter | 100 |
| 3RD DAY | Lab Analysis | 0 |

A one acre area containing large drilling mud pits was plowed and tilled. 55 gallons of first solution material as in Example 1 above was sprayed and tilled into the soil to a depth of eight inches to ten inches, with these results:

| DATE | TPH READING, ppm |
|---|---|
| 1ST DAY | 847.0 |
| 11TH DAY | 0.6 |

TEST 5

The area to be tested was a 15 by 30 foot area that was the site of a diesel spill and was also contaminated with other petroleum base products. Two different 3 feet by 10 feet areas were tilled and treated with 1.5 gallons of first solution material as in Example 1 above to a depth of six to eight inches with these results:

| | RESULTS | |
|---|---|---|
| | DATE | TPH READING, ppm |
| Site #1 (Initial) | 1ST DAY | 7100.0 |
| | 10TH DAY | 728.5 |
| | 29TH DAY | 345.6 |
| | 64TH DAY | 4.0 |
| Site #2 (Initial) | 1ST DAY | 7301.6 |
| | 10TH DAY | 1782.7 |
| | 29TH DAY | 854.0 |
| | 64TH DAY | 16.3 |

TEST 6

The area tested was the Site of a crude oil spill from salt water disposal tanks. The spill was approximately two years old and had soaked into the soil to a depth of 16 inches. Crude oil and brine were standing in pools on the entire area. An area 6 by 6 feet was tilled and 0.5 gallons of first solution material as in Example 1 above was sprayed evenly and mixed into the soil with these results:

| DATE | TPH READING, ppm |
|---|---|
| 1ST DAY | 54,426.0 |
| 10TH DAY | 9,895.2 |
| 31ST DAY | 13.7 |

The test area was substantially bioremediated in approximately 30 days.

TEST 7

One acre area that had been used as a tank battery and pit had primary contamination of crude oil to 18 inches in depth. The entire area had a strong smell of crude oil. The area was treated with 55 gallons of first solution material as in Example 1 above.

| DATE | TPH READING, ppm |
|---|---|
| 1ST DAY | 3572.2 |
| 10TH DAY | 7.6 |

One embodiment of material according to this invention as produced in Example 1 above had the following characteristics:

| | |
|---|---|
| Specific Gravity, g/cc | 1.0156 |
| Oil and Grease, ppm | <0.01 |
| Color | Dark Brown |
| Physical State | Liquid |
| Odor | Obnoxious |
| Layers | Bi-Layered |
| Ignitability, F (Pensky Martens Closed Cup) | >200 |
| Corrosivity, (pH) | 8.3 |
| Reactivity - S | No Reaction (<0.01 mg/l) |

-continued

| | |
|---|---|
| Reactivity - CN | No Reaction (<0.01 mg/l) |
| Total Solids (Dried Weight), % | 12.47 |
| APPEARANCE AFTER TWO TO FOUR HOURS | |
| Layers | 2 |
| Solids, % | 10 |
| Oil, % | <0.01 |
| Liquid, % | 90 |
| TCLP INORGANICS (Leachate) | |
| Arsenic, mg/l | <0.01 |
| Barium, mg/l | <0.05 |
| Cadmium, mg/l | <0.005 |
| Chromium, mg/l | 1.05 |
| Lead, mg/l | 0.02 |
| Mercury, mg/l | <0.002 |
| Selenium, mg/l | <0.01 |
| Silver, mg/l | <0.01 |
| Copper, mg/l | 0.03 |
| Nickel, mg/l | 0.12 |
| Zinc, mg/l | 0.11 |
| Thallium, mg/l | <0.06 |
| TCLP ORGANICS (e.g. insecticides & herbicides) | |
| Endrin | <0.005 |
| Lindane | <0.01 |
| Methoxychlor | <0.01 |
| Toxaphene | <0.01 |
| 2,4-D | <0.01 |
| 2,4,5-TP (Silvex) | <0.01 |
| Benzene | <0.01 |
| Carbon Tetrachloride | <0.01 |
| Chlordane | <0.01 |
| Chlorobenzene | <0.01 |
| Chloroform | <0.01 |
| o-Cresol | <0.01 |
| m-Cresol | <0.01 |
| p-Cresol | <0.01 |
| Cresol | <0.01 |
| 1,4-Dichlorobenzene | <0.01 |
| 1,2-Dichloroethane | <0.01 |
| 1,1-Dichlorethylene | <0.01 |
| 2,4-Dinitrotoluene | <0.01 |
| Heptachlor | <0.004 |
| Hexachlorobenzene | <0.01 |
| Hexachloro-1,3-butadiene | <0.01 |
| Hexachloroethane | <0.01 |
| Methyl Ethyl Ketone | <0.01 |
| Nitrobenzene | <0.01 |
| Pentachlorophenol | <0.01 |
| Pyridine | <0.01 |
| Tetrachlorethylene | <0.01 |
| 2,4,5-Trichlorophenol | <0.01 |
| 2,4,6-Trichlorophenol | <0.01 |
| Vinyl Chloride | <0.005 |

NOTE: Units expressed in mg/liter, unless otherwise noted.
METHOD:
HWC - EPA SW-846
TCLP INORGANICS (Leachate) - EPA 1311/7060/7080/7130/7190 7420/ 7471/7741/7760/7950 7210/7520/7841
TCLP ORGANICIS - EPA 8015/8020/8050/8080

In one process according to the present invention, any material according to this invention is applied to an ant mound or other insect or arachnid containing area. In one preferred embodiment about three ounces of first solution material produced as in Example 1 is mixed with about one gallon of water and the mixture is then poured on an ant mound.

In another process according to this invention about a gallon of material as in Example 2 above is mixed with a commercially available water soluble fertilizer, preferably one or more ounces of fertilizer, and is applied to house plants.

In another process according to this invention about forty or more gallons of material as in Example 2 are applied per acre to soil growing agricultural crops. Foliar application is also possible. E.g. about one quart of material as in Example 2 is mixed with about ten gallons of water and applied foliarly per acre to crops.

In another process according to this invention a remediation for salty soil is accomplished with a mixture as in Example 2 applied at about forty gallons per acre. In another process according to this invention remediation of soil contaminated with hydrocarbons is accomplished by treating the soil with a mixture as in Example 1 applied at about fifty gallons per acre. In another process according to the present invention a material as in Example 1 is applied to soil with a plant growing therein to stimulate the plant's growth and accelerate it to such an extent that the plant dies.

TEST 8

Soil contaminated with barium, cadmium, chromium, mercury, and lead was treated with the third solution (as previously described) by placing about eight ounces of the contaminated soil in a laboratory sample jar and treating it by misting about one and a half ounces of the treatment solution throughout the sample as the sample was stirred. A control sample was also made and isolated with no treatment. As received prior to treatment the contaminated soil had these levels, in milligrams per kilogram ("mg/Kg"), of the listed substances:

| | |
|---|---|
| arsenic | less than 1 |
| barium | 1810 |
| cadmium | 101 |
| chromium | 7550 |
| lead | 4880 |
| mercury | 2.1 |
| selenium | less than 1 |
| silver | less than 1 |

After treatment the treated sample had these levels of the listed substances:

| | |
|---|---|
| arsenic | less than 1 |
| barium | 697 |
| cadmium | 25 |
| chromium | 154 |
| lead | 1685 |
| mercury | 1.0 |
| selenium | less than 1 |
| silver | less than 1 |

The control sample showed no measurable difference in substance levels.

TEST 9

Soil from the Houston Ship Channel contaminated with chromium and lead was treated with the third solution (as previously described) by placing the about eight ounces of the contaminated soil sample in a laboratory sample jar and treating it by misting about one and a half ounces of the treatment solution throughout the sample while stirring the sample. A control sample was made and isolated without any treatment. The untreated soil had a pH of 11.52, chromium at a level of 542.68 mg/Kg, and lead at a level of 433.04 mg/Kg. After about one day the treated soil had a pH of 10.94, chromium at a level of 6.94 mg/Kg and lead at a level of 5,88 mg/Kg. After one day there was no change in these levels in the control sample.

TEST 10

Soil contaminated with barium, chromium, mercury, and lead was treated with the third solution (as previously described) by placing about eight ounces of the contaminated soil in a laboratory sample jar. The sample to be treated was stirred and misted throughout with about an ounce and a half of the treatment solution. A control sample was also made and isolated with no treatment. As received prior to treatment the contaminated soil had these levels, in milligrams per kilogram ("mg/Kg"), of the listed substances:

| lead | 178,000 |
|---|---|
| mercury | 5,670 |
| barium | 591 |
| chromium | 257 |

After treatment for one day the soil had these substance levels:

| lead | 12,000 |
|---|---|
| mercury | 2,520 |
| barium | 279 |
| chromium | 126 |

The control sample showed no measurable difference in substance levels after ten days.

TEST 11

Soil contaminated with garage waste oil from vehicles' crankcases contaminated with hydrocarbons and lead was treated with the third solution by placing it in an open dish nine inches in diameter and misting it with the treatment solution. The untreated sample initially had a lead level of about 132 mg/Kg and a hydrocarbon level of about 91,200 parts per million, i.e., about 13.5% hydrocarbons by volume. Also, the initial untreated oil had a total plate count of about 74,000 indigenous microorganisms per gram.

After 12 days, an untreated isolated control sample of the soil had substantially unchanged lead and hydrocarbon levels, and a total plate count of microorganisms of about 5,000,000 per gram. The treated soil had a lead level of about 94 mg/Kg, total hydrocarbons of about 36,900 parts per million and a total plate count of microorganisms of about 812,000,000 indigenous microorganisms. After 5 days of treatment the total plate count of microorganisms for the control sample was about 40,000,000 per gram and for the treated sample about 98,000,000 per gram.

TEST 12

Ballast rocks from a railroad right of way contaminated with Tall Oil were treated with the third solution (as previously described) by placing the rocks in a container with a total volume of about 32 ounces, the rocks occupying about fifty-five percent of the total volume. About 16 ounces of the solution were poured into the container. A commercially available fish aquarium aerator/bubbler was introduced beneath the surface of the solution and allowed to rest on the bottom of the container with bubbles of air (about 2 to 3 p.s.i. lab air supply) bubbling up from it. A control sample was placed in a jar and isolated without any treatment.

The oil and grease level (hydrocarbon contamination level) of the untreated rocks was 13,300 ppm. After three days of treatment the level of hydrocarbons was about 5600 ppm and after 5 days of treatment the level was about 1790 ppm. The level for the control sample remained substantially unchanged.

In one preferred embodiment of the third solution, the pH is about 8.6, the electroconductivity is 12.93 ds/cm, total organic compounds by volume is about 8.8% and the substances listed below have the levels indicated

| nitrogen | .24% by volume |
|---|---|
| phosphorous | .028% by volume |
| potassium | 1.034% by volume |
| calcium | .19% by volume |
| magnesium | .032% by volume |
| iron | 524.5 parts per million |
| manganese | 5.9 parts per million |
| copper | 1.5 parts per million |
| zinc | 13.8 parts per million |
| sodium | 960.0 parts per million |

By homogenizing the base solution (as previously described) either once following production or during recirculation of the material during production, more concentrated solutions may be produced according to this invention—more concentrated with respect to the level of organic acids by volume in the final product. In one embodiment of the base solution (as previously described) the level of humic acid and other organic acids combined (including fulvic, ulvic, alginic, and polyuronic) is about 32%.

Any of the solutions according to this invention may be dehumidified to produce a powder according to this invention. In one method the solution is sprayed onto a drying surface, permitted to dry to a powder, and then the powder is collected and put in containers. The powder may be mixed with water and then applied or the powder may be applied and then water is added or applied.

In the tests and examples described above no additional microorganisms were added to the treating solution or to the contaminated material. However, it is within the scope of this invention to add additional microorganisms—either those indigenous to the contaminated material or not.

Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized.

What is claimed is:

1. A treatment composition for treating contaminated material, the treatment composition comprising water, powderized soft coal, an alkali metal carbonate, and algin extract solution, the ratio by weight of water to coal to alkali metal carbonate about 18:6:1.

2. The treatment composition of claim 1 wherein the ratio by volume of algin extract solution to combined water, coal and alkali metal carbonate is about 1:1.

3. A treatment composition for treating contaminated material, the treatment composition comprising water, powderized soft coal, and flaked potash, the ratio by weight of water to coal to flaked potash about 24:6:1.

4. A method for making a liquid treatment composition for treating contaminated material, the method comprising introducing water into a first tank, blending in alkali metal carbonate in the first tank with the water to form a first composition, adding coal to the first composition and blending them together forming a liquid base composition, introducing one half of the liquid base composition from the first tank into a second tank, introducing an amount of seaweed derivative into the second tank equal in volume to the volume of the one half of the liquid base composition from the first tank, and blending the contents of the second tank together producing a liquid treatment composition.

5. The method of claim 4 wherein the water is introduced into the first tank with a temperature between about 72 and about 110 degrees F. and the ratio by weight of water to coal to alkali metal carbonate in the base composition is about 18:6:1.

6. The method of claim 4 wherein the coal is powderized soft coal, the alkali metal carbonate is flaked potash, and the seaweed derivative is algin extract solution.

7. A method for making a liquid treatment composition for treating contaminated material, the method comprising introducing water into a first tank, blending in alkali metal carbonate in the first tank with the water to form a first composition, adding coal to the first composition and blending them together forming a liquid base composition, introducing one half of the liquid base composition from the first tank into a second tank, introducing an amount of seaweed derivative into the second tank equal in volume to the volume of the one half of the liquid base composition from the first tank, blending the contents of the second tank together producing blended contents, and diluting the blended contents with about 35% water by volume and blending the diluted blended contents of the second tank together producing a liquid treatment composition.

8. A method for making a liquid treatment composition for treating contaminated material, the method comprising introducing water into a first tank, blending in alkali metal carbonate in the first tank with the water to form a first composition, adding coal to the first composition and blending them together forming a liquid base composition, introducing one half of the liquid base composition from the first tank into a second tank, introducing an amount of seaweed derivative into the second tank equal in volume to the volume of the one half of the liquid base composition from the first tank, blending the contents of the second tank together producing blended contents, and blending three parts of the blended contents of the second tank with another one part seaweed derivative to produce a liquid treatment composition.

* * * * *